(12) United States Patent
Lee et al.

(10) Patent No.: US 7,670,831 B2
(45) Date of Patent: Mar. 2, 2010

(54) CONDUCTIVE CARBON NANOTUBES DOTTED WITH METAL AND METHOD FOR FABRICATING A BIOSENSOR USING THE SAME

(75) Inventors: Sang Yup Lee, Daejeon (KR); Hee Tae Jung, Daejeon (KR); Dae Hwan Jung, Daejeon (KR); Young Koan Ko, Daejeon (KR); Do Hyun Kim, Daejeon (KR); Seok Jae Lee, Daejeon (KR); Byung Hun Kim, Seoul (KR); Jae Shin Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 972 days.

(21) Appl. No.: 10/860,544

(22) Filed: Jun. 3, 2004

(65) Prior Publication Data

US 2010/0009432 A1      Jan. 14, 2010

(30) Foreign Application Priority Data

Jun. 13, 2003    (KR)    ............... 10-2003-0038183
Jun. 13, 2003    (KR)    ............... 10-2003-0038232

(51) Int. Cl.
| | |
|---|---|
| *C12M 1/00* | (2006.01) |
| *C12Q 1/00* | (2006.01) |
| *C12Q 1/68* | (2006.01) |
| *C12M 1/34* | (2006.01) |

(52) U.S. Cl. ............... 435/283.1; 435/4; 435/6; 435/7.1; 435/287.2; 977/742; 977/745; 977/746; 977/747; 977/748

(58) Field of Classification Search ............ 435/4, 435/6, 7.1, 283.1; 977/742, 745, 746, 747, 977/748

See application file for complete search history.

(56) References Cited

U.S. PATENT DOCUMENTS

| | | | | |
|---|---|---|---|---|
| 5,474,895 | A * | 12/1995 | Ishii et al. ............ | 435/6 |
| 5,866,434 | A * | 2/1999 | Massey et al. ........ | 436/526 |
| 6,872,681 | B2 | 3/2005 | Niu et al. | |
| 7,272,511 | B2 | 9/2007 | Occhipinti et al. | |
| 2002/0172963 | A1* | 11/2002 | Kelley et al. ........ | 435/6 |
| 2002/0179434 | A1* | 12/2002 | Dai et al. ............ | 204/242 |
| 2003/0012723 | A1* | 1/2003 | Clarke ................. | 423/460 |
| 2004/0028901 | A1 | 2/2004 | Rumpf et al. | |
| 2004/0142285 | A1 | 7/2004 | Jung et al. | |
| 2004/0235016 | A1* | 11/2004 | Hamers et al. ....... | 435/6 |
| 2005/0019791 | A1 | 1/2005 | Jung et al. | |
| 2005/0214195 | A1 | 9/2005 | Jung et al. | |
| 2006/0003401 | A1 | 1/2006 | Lee et al. | |

FOREIGN PATENT DOCUMENTS

| | | |
|---|---|---|
| KR | 20050012050 A | 1/2005 |
| KR | 20050013006 A | 2/2005 |
| WO | WO 96/07487 * | 3/1996 |
| WO | WO 02/086168 | 10/2002 |
| WO | WO 03/016901 A1 | 2/2003 |

OTHER PUBLICATIONS

Mamedov et al, Molecular design of strong single-wall carbon nanotube/polyelectrolyte multilayer composites, 2002, Nature materials, 1, 190-194.*

Alexandre, I., et al.; Colorimetric Silver Detection of DNA Microarrays; Analytical Biochemistry; 2001; vol. 295, pp. 1-8; Academic Press; USA.

Azamian, Bobak R., et al.; Bioelectrochemical Single-Walled Carbon Nanotubes; JACS Communications; 2002, 124, pp. 12664-12665; American Chemical Society; USA.

Houseman, Benjamin T., et al.; Towards quantitative assays with peptide chips: a surface engineering approach; TRENDS in Biotechnology; 2002; vol. 20, No. 7; pp. 279-281; Elsevier Science Ltd.; USA.

Cai, Hong, et al.; Carbon nanotube-enhanced eletrochemical DNA biosensor for DNA hybridization detection; Anal. Bioanal. Chemistry; 2003; 375; pp. 287-293; East China Normal University, Department of Chemistry; China.

Cai, Hong, et al.; An electrochemical DNA hybridization detection assay based on a silver nanoparticle label; The Analyst; 2002; vol. 127; pp. 803-808; The Royal Society of Chemistry 2002; China.

Chen, Jiyan, et al.; Lifetime- and Color-Tailored Fluorophores in the Micro- to Millisecond Time Regime; J. Am. Chem. Soc.; 2000; vol. 122; pp. 657-660; American Chemical Society; USA.

Chen, Robert J., et al.; Noncovalent functionalization of carbon nanotubes for highly specific electronic biosensors; PNAS; 2003; vol. 100, No. 9, pp. 4984-4989; Stanford University; USA.

Dähne, Lars, et al.; Fabrication of Micro Reaction Cages with Tailored Properties; J. Am. Chem. Soc.; 2001; vol. 123; pp. 5431-5436; American Chemical Society; USA.

Dai, Hongjie; Carbon Nanotubes: Synthesis, Integration, and Properties; Acc. Chem. Res.; 2002; vol. 35, No. 12, pp. 1035-1044; Stanford University; USA.

(Continued)

*Primary Examiner*—BJ Forman
*Assistant Examiner*—Narayan K Bhat
(74) *Attorney, Agent, or Firm*—Kelly K. Reynolds; Steven J. Hultquist

(57) ABSTRACT

Conductive carbon nanotubes (CNTs) obtained by dotting carboxylated CNTs with metal nanocrystals by chemical functional groups, are described, as well as a method for fabricating a pattern or film of the conductive CNTs which involves repeatedly depositing conductive CNTs on a substrate to achieve high surface density. A biosensor is described, in which bioreceptors that bind to target biomolecules are selectively attached to conductive CNTs or a conductive CNT pattern or film. By use of the conductive biosensor, various target biomaterials that bind or react with the bioreceptors can be precisely measured directly or by electrochemical signals at large amounts in one step. Additionally, the biosensor can be used for an electrical detection method capable of providing precise measurement results even with a small amount of source material.

8 Claims, 12 Drawing Sheets

OTHER PUBLICATIONS

Erlanger, Bernard F., et al.; Binding of an Anti-Fullerence IgG Monoclonal Antibody to Single Wall Carbon Nanotubes; Nono Letters; 2001; vol. 1, No. 9, pp. 465-467; American Chemical Society; USA.

Grow, Ann E., et al.; New biochip technology for label-free detection of pathogens and their toxins; Journal of Microbiological Methods; 2003; Vole. 53; pp. 221-233; Elsevier Science B.V.; USA.

Hergenrother, Paul J., et al.; Small-Molecule Microarrays: Covalent Attachment and Screening of Alcohol-Containing Small Molecules on Glass Slides; J. Am. Chem. Soc.; 2000; vol. 122; pp. 7849-7850; American Chemical Society; USA.

Hu, Jian, et al.; The ARKdb: genome databases for farmed and other animals; Nucleic Acids Research 2001; vol. 29, No. 1; pp. 106-110; Oxford University Press; USA.

Jiang, Kuiyang, et al.; Selective Attachment of Gold Nanoparticles to Nitrogen-Doped Carbon Nanotubes; Nano Letters; 2003; vol. 3, No. 3; pp. 275-277; American Chemical Society; USA.

Kouwenhoven, Leo; Single-Molecule Transistors; Science; 1997; vol. 275, Issue 5308; pp. 1896-1897; Korea.

Li, Jun, et al.; Carbon Nanotube Nanoelectrode Array for Ultrasensitive DNA Detection; Nano Letters; 2003; vol. 3, No. 5; pp. 597-602; American Chemcial Society; USA.

Matsushige, K., et al.; Nanoscale control and detection of electric dipoles in organic molecules; Nanotechnology 9; 1998; pp. 208-211; IOP Publishing Ltd.; USA.

Nan, Xiaolin, et al.; Immobilizing Shortened Single-Walled Carbon Nanotubes (SWNTs) on Gold Using a Surface Condensation Method; Journal of Colloid and Interface Science; 2002; vol. 245; pp. 311-318; Elseview Science; USA.

Rogers, Yu-Hui, et al.; Immobilization of Oligonucleotides onto a Glass Support via Disulfide Bonds: A Method for Preparation of DNA Microarrays; Analytical Biochemistry; 1999; vol. 266; pp. 23-30; Academic Press; USA.

Rouse, Jason H., et al.; Electrostatic Assembly of Polymer/Single Walled Carbon Nanotube Multilayer Films; Nano Letters; 2003; vol. 3. No. 1; pp. 59-62; American Chemical Society; USA.

Schena, Mark, et al.; Quantitative Monitoring of Gene Expression Patterns with a Complementary DNA Microarray; Science; 1995; vol. 270; pp. 467-470; USA.

Star, Alexander, et al.; Electronic Detection of Specific Protein Binding Using Nanotube FET Devices; Nano Letters; 2003; vol. 3, No. 4; pp. 459-463; American Chemical Society; USA.

Sotiropoulou, Sofia, et al.; Carbon nanotube array-based biosensor; Anal Bioannal Chem; 2003; vol. 375; pp. 103-105; University of Crete; Greece.

Stelzle, M., et al.; On the Application of Supported Bilayers as Receptive Layers for Biosensors with Electrical Detection; J. Phys. Chem; 1993; vol. 97; pp. 2974-2981; American Chemical Society; USA.

Syrzycka, Monika, et al.; Electronic concentration of negatively-charged molecules on a microfabricated biochip; Analytica Chimica Acta; 2003; vol. 484; pp. 1-14; Elsevier Science B.V.; Canada.

Taton, J. Andrew; et al.; Scanometric DNA Array Detection with Nanoparticle Probes; Science; 2000; vol. 289; pp. 1757-1760; USA.

Toriba, Akira, et al.; Quantification of polycyclic aromatic hydrocarbons (PAHs) in human hair by HPLC with fluorescence detection: a biological monitoring method to evaluate the exposure to PAHs; Biomedical Chromatography; 2003; Vp;. 17; pp. 126-132; John Wiley & Sons, Ltd.; USA.

Vijayendran, Ravi A., et al.; A Quantitative Assessment of Heterogeneity for Surface-Immobilized Proteins; Analytical Chemistry; 2001; vol. 73; pp. 471-480; American Chemical Society; USA.

Williams, Keith A., et al.; Carbon nanotubes with DNA recognition; Nature; 2002; vol. 420; p. 761; Nature Publishing Group; USA.

Bandyopadhyaya, R. et al., "Stabilization of Individual Carbon Nanotubes in Aqueous Solutions", Nov. 22, 2001, pp. 25-28, vol. 2, No. 1.

Bockwrath, M. et al., "Single Electron Transport in Ropes of Carbon Nanotubes", "Science", Mar. 28, 1997, pp. 1922-1925, vol. 275.

Chambers, G. et al., "Characterization of the Interaction of Gamma Cyclodextrin with Single Walled Carbon Nanotubes," "Nano Letters", Apr. 19, 2003, pp. 843-846, vol. 3, No. 6, Publisher: American Chemical Society.

Chen, J. et al. , "Solution Properties of Single Walled Carbon Nanotubes", "Science", Oct. 2, 1998, pp. 95-98, vol. 282.

Chen, J. et al., "Noncovalent Engineering of Carbon Nanotube Surfaces by Rigid Functional Conjugated Polymers", "J. Am. Chem. Society Communications", Jul. 13, 2002, pp. 9034-9035, vol. 124.

Chiu, P.W. , "Interconnection of Carbon Nanotubes by Chemical Functionalization", May 20, 2002, pp. 3811-3813, vol. 80, No. 20.

Dai, H., "Carbon Nanotubes: Synthesis, Integration, and Properties", "Acc. Chem. Res.", Aug. 7, 2002, pp. 2002 vol. 35, No. 12, Publisher: American Chemical Society.

Georgakilas, V. et al., "Amino Acid functionalisation of water soluble carbon nanotubes", "Chem. Commun.", Nov. 14, 2002, pp. 3050-3051.

Kang, Y. et al., "Micelle encapsulated Carbon Nanotubes: A Route to Nanotube Composites", "J. AM. Chemical Society", Apr. 19, 2003, pp. 5650-5651, vol. 125.

Mitchell, C. et al., "Dispersion of Functionalized Carbon Nanotubes in Polystyrene", "Macromolecules", Sep. 28, 2002, pp. 8825-8830, vol. 35, Publisher: American Chemical Society.

Moll, D. et al. , "S-layer streptavidin fusion proteins as template for nanopatterned molecular arrays", "PNAS", Nov. 12, 2002, pp. 14646-14651, vol. 99, No. 23.

Nan, A. et al., "Immobilizing Shortened Single Walled Carbon Nanotubes (SWNTs) on Gold Using A Surface Condensation Method", "Journal of Colloid and Interface Science", 2002, pp. 311-318, vol. 245.

Oconnell, M. et al., "Reversible water solubilization of single walled carbon nanotubes by polymer wrapping", "Chemical Physical Letters", Jul. 31, 2001, pp. 265-271, vol. 342, Publisher: Elsevier.

Pantarotto, D. et al., "Immunization with Peptide-Functionalized Carbon Nanotubes Enhances Virus Specific Neutralizing Antibody Responses", "Chemistry and Biology", Oct. 2003, pp. 961-966, vol. 10.

Pum, D. et al., "The application of bacterial S-layers in molecular nanotechnology", "Nanotechnology", Jan. 1999, pp. 8-, vol. 17.

Rao, A. et al. , "Diameter Selective Raman Scattering from Vibrational Modes in Carbon Nanotubes", "Science", Jan. 10, 1997, pp. 187-191, vol. 275.

Rouse, J. et al., "Electrostatic Assembly of Polymer / Single Walled Carbon Nanotube Multilayer Films", "Nano Letters", Dec. 5, 2002, pp. 56-62, vol. 3, No. 1, Publisher: American Chemical Society.

Star, A. et el., "Dipsersion and Solubilization of Single Walled Carbon Nanotubes with a Hyperbranched Polymer", "Macromolecules", Aug. 8, 2002, pp. 7516-7520, vol. 35.

* cited by examiner

Hybridization with complementary DNA

Hybridization with non-complementary DNA

CONDUCTIVE CARBON NANOTUBES DOTTED WITH METAL AND METHOD FOR FABRICATING A BIOSENSOR USING THE SAME

CROSS-REFERENCE TO RELATED APPLICATIONS

This application claims priority under 35 USC 119 of Korean Patent Application No. 10-2003-0038232 filed Jun. 13, 2003 and Korean Patent Application No. 10-2003-0038183 filed Jun. 13, 2003.

BACKGROUND OF THE INVENTION

1. Field of the Invention

The present invention relates to conductive carbon nanotubes (CNTs) obtained by dotting carboxylated carbon nanotubes with metal nanocrystals by chemical functional groups. Also, the invention relates to a method for fabricating a conductive CNT pattern or film, which comprises repeatedly depositing such conductive CNTs on a substrate to have high surface density. Moreover, the invention relates to a biosensor wherein bioreceptors that bind to target biomolecules are selectively attached to the conductive CNTs or the conductive CNT pattern or film, as well as to a fabricating method for such biosensor.

2. Background of the Related Art

Carbon nanotube (CNT) is an allotrope of carbon, which is composed of carbons that exist abundantly on the earth. CNTs are tubular materials in which a carbon atom is connected to other carbons in the form of a hexagonal honeycomb structure. Their diameter is about the size of nanometer ($1/10^9$ meter). CNT is known to have excellent mechanical properties, electrical selectivity, field emission properties and highly efficient hydrogen storage properties and is substantially defect-free in character.

CNT in consequence of such attributes has virtually limitless applicability in the fields of electron emitters, vacuum fluorescent displays (VFD), white luminous sources, field emission displays (FED), lithium ion secondary battery electrodes, hydrogen storage fuel cells, nano-wires, nano-capsules, nano-tweezers, AFM/STM tips, single electron devices, gas sensors, medical engineering microscopic parts, etc.

Because of their properties of excellent structural rigidity, chemical stability, and ability to act as ideal one-dimensional (1D) "quantum wires" with either semiconducting or metallic behaviors and a large aspect ratio, CNT exhibits a broad range of potential applications as a basic material of flat panel displays, transistors, energy reservoirs, etc., and as various sensors with nanosize (Dai, H., *Acc. Chem. Res.*, 35:1035, 2002).

In order to apply such properties more diversely, the purified single-walled CNT has been cut into short nanotube pieces using an acid. The cut CNT pieces have mainly —COOH chemical functional groups at a part of ends and sidewall of the open tube. The properties of the CNT have been modified by chemical binding of various materials using these chemical functional groups. Further, substitution of the functional group of CNT for an —SH group by chemical manipulation and patterning on a gold surface using a microcontact printing method has been reported (Nan, X. et al., *J. Colloid Interface Sci.*, 245:311, 2002). CNT immobilization on a substrate in a multilayered film using an electrostatic method has also been reported (Rouse, J. H. et al., *Nano Lett.*, 3:59, 2003). The first-mentioned substitution method has disadvantages of low CNT surface density and weak bonding, and the second-mentioned CNT immobilization method also has the fatal disadvantage that the patterning method for selective immobilization on the surface cannot be applied. Therefore, there is an urgent need for a new type of surface immobilizing method that achieves high density.

Since most diseases are caused at a protein level other than a genetic level, more than 95% of medical drugs developed to date or in current development, target a protein. Thus, technologies for the detection of protein-protein and protein-ligand interactions are necessary in studies to establish the function of biomolecules interacting with certain proteins and ligands and to develop therapeutic and preventive methods against diseases. The development of such technologies by classical techniques, based on data obtained by protein function analysis and network analysis, has not been successful in providing a simple, economic, effective and reliable method for detection of protein-protein and protein-ligand interactions.

The technology for the detection of protein-protein interaction, as heretofore practiced, is a protein-chip technology. This is a technology in which the orientation of biomolecules is controlled at a molecular level using an affinity tag for a target protein, to specifically immobilize a uniform stable monolayer of protein on the surface of a substrate, followed by the analysis of the protein-protein interaction (Hergenrother, P. J. et al., *JACS*, 122:7849, 2000; Vijayendran, R. J., A. et al., *Anal. Chem.*, 73:471, 2001; Benjamin, T. et al., *Tibtech.*, 20:279, 2002).

Recently, research has been directed to the detection of both protein-protein and protein-ligand reactions by means of electrochemical changes of CNT after immobilization of a biomaterial (Dai, H. et al., *ACC. Chem. Res.*, 35:1035, 2002; Sotiropoulou, S. et al., *Anal. Bioanal. Chem.*, 375:103, 2003; Erlanger, B. F. et al., *Nano Lett.*, 1:465, 2001; Azamian, B. R. et al., *JACS*, 124:12664, 2002). A representative example of a protein-ligand reaction is an avidin-biotin reaction. In one reported effort, a channel was formed on a substrate that had been treated with a polymer, using CNT and the binding activity of streptavidin was measured by means of an electrochemical method (Star, A. et al., *Nano Lett.*, 3:459, 2003).

The methods of preparing a high density CNT structure, attaching DNA thereon and detecting complementary DNA are useful in genotyping, mutation detection, pathogen identification and the like. It has been reported that PNA (peptide nucleic acid: DNA mimic) is regio-specifically fixed on a single walled CNT and complementary binding to probe DNA is detected (Williams, K. A. et al., *Nature*, 420:761, 2001). The fixture of an oligonucleotide on a CNT array by an electrochemical method and detection of DNA by guanidine oxidation also has been reported (Li, J. et al., *Nano Lett.*, 3:597, 2003). However, these methods do not apply CNT to fabrication and development of biochips.

Recently, a high capacity biomolecule detection sensor using CNT has been disclosed (WO 03/016901 A1). This patent publication relates to a multi-channel type biochip produced by arranging a plurality of CNTs on a substrate using a chemical linker and attaching various types of receptors. However, it has the disadvantage that precision analysis is not achieved, due to the relative weakness of electric conductivity of the sensor.

The reasons that CNT attracts public attention as a biochip material include the following: firstly, CNT needs no labeling; secondly, CNT has high sensitivity to signal change; and thirdly, CNT is capable of reacting in an aqueous solution without deterioration of a protein. The combination of a new nanomaterial and a biological system will create important fusion technologies in a large number of fields, including disease diagnosis (hereditary diseases), proteomics and nanobiotechnology.

A large amount of genetic information was obtained by the Human Genome Project, and this information has provided a stepping-stone that will lead to innovation in the understanding and diagnosis of genetic diseases. In this effort, the development of an effective DNA fingerprinting system for genomic sequencing, mutation detection and pathogen identification is needed.

In order to develop a faster and cheaper biosensor, substantial research efforts have been focused on technologies of DNA hybridization detection. Various labeling techniques for detecting DNA hybridization have been developed. Currently, fluorescent substances are most generally used in labeling. A single DNA chain capable of detecting complementary DNAs is immobilized to recognize complementary DNAs in aqueous solution, and a signal transducer changes a DNA hybridization signal into an analyzable signal.

Regarding the signal transducers, optical (fluorescent), piezoelectric and electrochemical transduction techniques are being studied. Among these, the electrochemical technique has various advantages, including high sensitivity, low cost and compatibility with microfabrication technology, and it can detect DNA having specific base sequences in a rapid and direct manner.

There are several methods capable of immobilizing a DNA probe on a transducer surface. These methods can be classified into several categories, including chemical adsorption, covalent-binding, electrostatic attraction, co-polymerization, and avidin-biotin affinity approaches. Also, DNAs may be immobilized on a micrometer-sized surface using a conductive polymer.

An effective surface treatment capable of increasing hybridization efficiency and simultaneously, removing the background from non-specific binding, is required to detect the DNA hybridization effectively using a DNA chip. Much research has been conducted to prepare a surface-treated DNA chip platform (Rogers, Y. et al., *Anal. Biochem.*, 266:23, 1999; Hu, J. et al., *Nuc. Acid. Res.*, 29:106, 2001). Also, various methods for detecting DNA hybridization have been developed, which include the scanometric method, the calorimetric method, a nanoparticle method, an electrochemical method, and etc. (Taton, T. A. et al., *Science*, 289:1757, 2000; Alexandre, I. et al., *Anal. Biochem.*, 295:1, 2001; Cai, H. et al., *Analyst.*, 127:803, 2002; Cai, H. et al., *Anal. Bioanal. Chem.*, 375:287, 2003).

Additionally, many applications of CNT in the bioengineering field have recently begun appearing in the literature, including application of CNT to biochips, such as glucose biosensors, detecting protein, detecting a certain DNA sequence, and the like (Sotiropoulou, S. et al., *Anal. Bioanal. Chem.*, 375:103, 2003; Chen, R. J. et al., *Proc. Natl. Acad. Sci. USA*, 100:4984, 2003; Cai, H. et al., *Anal. Bioanal. Chem.*, 375:287, 2003). Screening bio-molecules from a multilayer based on CNT can increase the amount of immobilized bio-substances, such as DNAs, and can increase the detection sensitivity to the bio-substances, since multilayer structures based on CNT have wide surface area and high electric conductivity.

The recent efforts to combine biotechnology (BT) with nanotechnology (NT) has accelerated the development of hybrid nanomaterials using the property of biomaterials that can specifically bind. DNAs are of particular interest as smart nanowires that can bind to the desired locations.

The combination of information technology (IT), NT and BT has made it possible to employ quick and precise digital information in the measurement of analog data, such as the presence or absence of biomaterials, and reactivity, by electrical detection methods (Chen, J. et al., *JACS*, 122:657, 2000; Dahne, L. et al., *JACS*, 123:5431, 2001).

A lipid-protein double layer which was first examined has electrical properties. Thus, it was used in cell immobilization to study cell surface characteristics and cell interactions. A more practical application has used a receptor layer as a biosensor for optical and electrical detection. In 1993, German Stelzle, M. et al. reported its possibility as a biosensor by impedance analysis in a sensor based on two layers of lipid/receptor (Stelzle, M. et al., *J. Phys. Chem.*, 97:2974, 1993). Furthermore, in the field of detecting smaller molecules by electrical methods, a study result was reported indicating that the directions of electric dipoles in organic molecules can be controlled in nanoscale by applying electric pulses to a probe, such as an atomic force microscope (AFM). According to this study, if the probe is coated with a suitable metal to confer electrical properties, and electric pulses with changed polarity are applied to the organic molecules from the probe, high-density molecular memory chips, such as devices, can be fabricated, and electric charge of organic molecules can also be measured by this approach (Matsushige, K. et al., *Nanotechnol.*, 9:208, 1998).

An international patent application relating to methods of comparing the relative contents of biomolecules and identifying biomolecules in a sample with affinity tags and mass spectrometry was recently published (WO 2002/86168 A1).

At present, the most universal method for detecting the result of a reaction in a biochip is to use conventional fluorescent materials and isotopes (Toriba, A. et al., *Biomed. Chromatogr.*, 17:126, 2003; Syrzycka, M. et al., *Anal. Chim. Acta*, 484:1, 2003; Grow, A. E. et al., *J. Microbio. Meth.*, 53:221, 2003). However, as novel methods to more readily and precisely measure an electrical or electrochemical signal develop, there are increased demands for CNT as a new material.

SUMMARY OF THE INVENTION

The present invention in one aspect provides CNTs that are dotted with a metal, and thus have excellent electrical conductivity. The invention also contemplates methods of making such CNTs.

The invention in another aspect provides a method for forming a CNT pattern by depositing metal-dotted CNTs on a substrate.

In yet another aspect, the invention provides a CNT film having high surface density and excellent electrical conductivity.

A further aspect of the invention relates to a conductive CNT-biosensor in which a variety of bioreceptors are attached to the conductive CNTs, the conductive CNT pattern or film. The invention in such aspect also contemplates a method of making such conductive CNT-biosensor device.

In another aspect, the invention provides a method for detecting various target biomaterials that bind to or react with various bioreceptors, using a CNT-biosensor.

BRIEF DESCRIPTION OF THE DRAWINGS

FIG. 3 is a flow chart illustrating a method for fabricating a pattern of CNTs dotted with gold nanoparticles.

FIG. 12 is a schematic diagram showing that DNA binds to a CNT dotted with gold nanoparticles to form a CNT-Au-DNA complex.

FIG. 13 is a photograph showing that DNAs having thiol functional groups are attached to CNTs dotted with gold nanoparticles.

DETAILED DESCRIPTION OF THE INVENTION, AND PREFERRED EMBODIMENTS THEREOF

Figure 1:
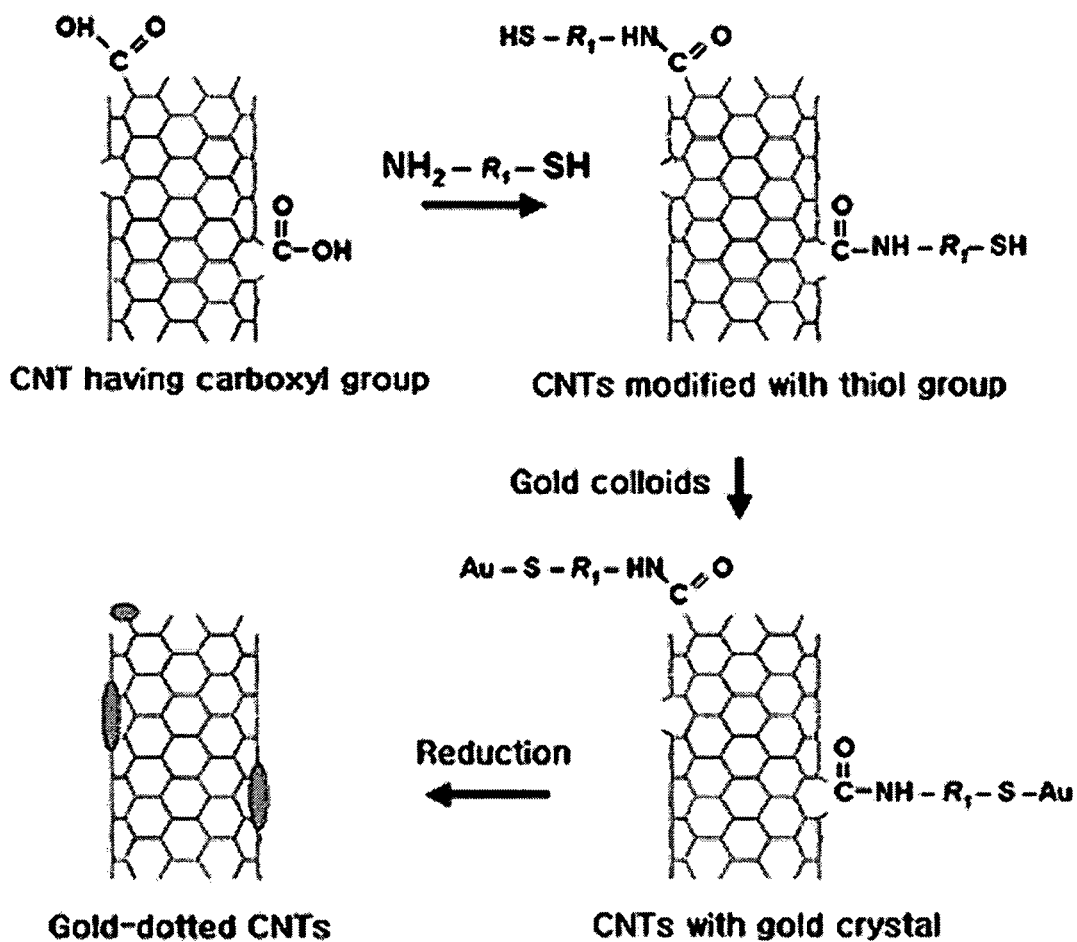
FIG. 1 is a schematic diagram showing a process for producing carbon nanotubes (CNTs) dotted with gold nanoparticles.
Figure 2:
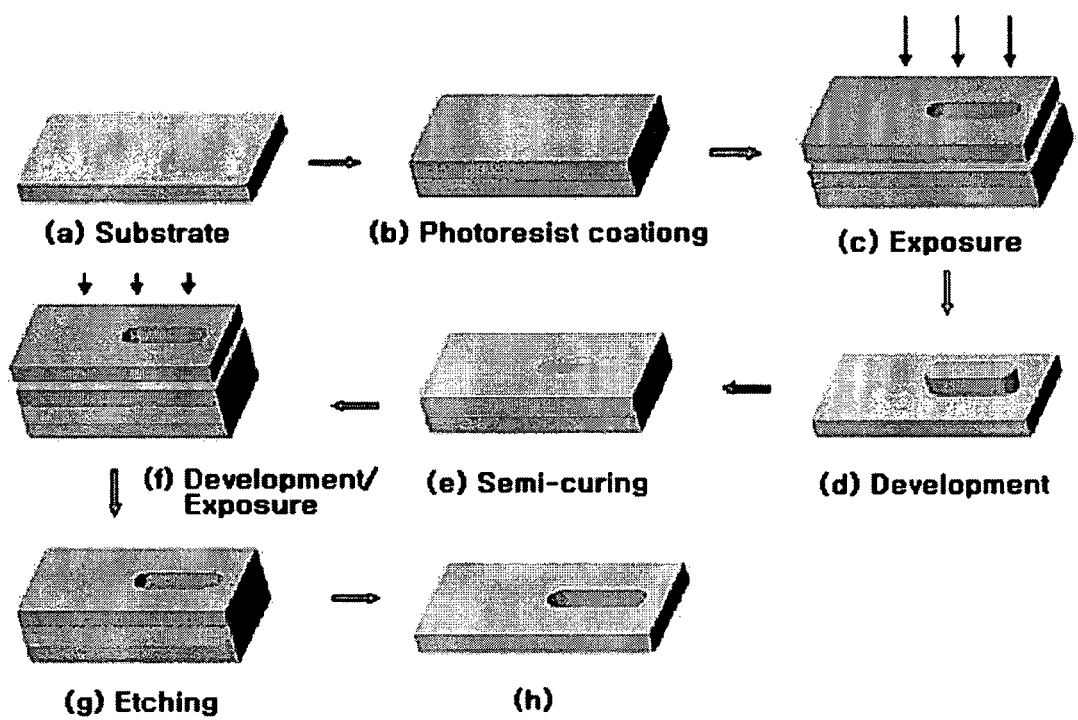
FIG. 2 is a schematic diagram showing a process for making a polymer mask pattern having a given shape for the integration of CNTs of FIG. 1 on a silicon substrate by photolithography.

The present invention in one aspect provides a method for producing conductive CNTs dotted with a metal, which includes the steps of: (a) providing CNTs having a carboxyl group; (b) binding the carboxyl group of the CNTs to an amino group of a chemical substance having amino and thiol groups, to obtain CNTs modified with the thiol group; and (c) binding a metal to the thiol group of the thiol group-modified CNTs.

In such method, the chemical substance having both amino and thiol groups is preferably an amino-thiol compound of the formula $NH_2$—$R_1$—SH wherein $R_1$ represents divalent $C_{1-20}$ saturated hydrocarbons, unsaturated hydrocarbons or aromatic organic groups. Step (a) of such method is preferably performed by treating the CNTs with an acid, and the metal is preferably gold. Step (c) is preferably carried out by reacting the thiol group-modified CNTs with metal nanoparticles or colloids, and then subjecting the resulting CNTs to reduction.

In another aspect, the present invention provides conductive CNTs dotted with a metal, in which the CNTs have a form of CNT-(CONH—$R_1$—S-M)r wherein M represents a metal, $R_1$ is as identified above, and r is a natural number greater than 1. The metal is preferably gold.

In still another aspect, the present invention provides a method for fabricating a conductive CNT pattern, which comprises the steps of: (a) providing a substrate having thiol groups exposed on a surface thereof in a form of pattern; (b) binding the metal of metal-dotted conductive CNTs to the thiol groups on the substrate surface; (c) binding metal-dotted conductive CNTs to the bound CNTs, to deposit the CNTs; and (d) repeating the step (c). Also, the present invention provides a conductive CNT pattern which is fabricated by this method and has a structure of substrate-[CONH—$R_2$—S-M-CNT-M-(S—$R_3$—S-M-CNT-M)p]q wherein p and q are natural numbers greater than 1.

In another aspect, the present invention provides a method for fabricating a conductive CNT film, which comprises the steps of: (a) providing a substrate having thiol groups exposed on its surface; (b) binding the metal of metal-dotted CNTs to the thiol groups on the substrate surface; (c) binding the conductive CNTs to the conductive CNTs attached to the substrate, to deposit the conductive CNTs; and (d) repeating the step (c), to increase the density of the conductive CNTs. Also, the present invention provides a conductive CNT film, which is fabricated by this method and has a structure of substrate-[CONH—$R_2$—S-M-CNT-M-(S—$R_3$—S-M-CNT-M)p]q, wherein p and q are natural numbers greater than 1.

In the step (a) of the inventive method as described just above, a substrate having amino functional groups exposed on its surface is preferably treated with a chemical substance having both carboxyl and thiol groups, to form amide bonds between the amino groups on the substrate and the carboxyl groups of the chemical substance. The chemical substance having both carboxyl and thiol groups is preferably a substance represented by the formula HOOC—$R_2$—SH wherein $R_2$ signifies divalent $C_{1-20}$ saturated hydrocarbons, unsaturated hydrocarbons or aromatic organic groups. The substrate having amino functional groups exposed on its surface is preferably obtained by treating a certain substrate with aminoalkyloxysilane.

The binding between the amino groups and the carboxyl groups is preferably performed using a coupling agent and a base, and the step (c) is preferably performed using a linker having double thiol functional groups. The linker having double thiol functional groups is preferably HS—$R_3$—SH, wherein $R_3$ represents divalent $C_{1-20}$ saturated hydrocarbons, unsaturated hydrocarbons or aromatic organic groups. Also, in order to attach the conductive CNTs to the desired locations, the substrate preferably has a photoresist or polymer pattern formed thereon, and is selected from the group consisting of glass, silicon, molten silica, plastic and PDMS.

In another aspect, the present invention provides a conductive CNT-biosensor in which a bioreceptor that binds to or reacts with target biomaterials is attached to any one selected from the group consisting of the following: (a) conductive CNTs having a structure of CNT-(CONH—$R_1$—S-M)r wherein M represents a metal, r is a natural number greater than 1, and $R_1$ represents $C_{1-20}$ saturated hydrocarbons, unsaturated hydrocarbons or aromatic organic groups; (b) a conductive CNT pattern having a structure of substrate-[CONH—$R_2$—S-M-CNT-M-(S—$R_3$—S-M-CNT-M)p]p wherein p and q are natural numbers greater than 1, $R_2$ and $R_3$ represent $C_{1-20}$ saturated hydrocarbons, unsaturated hydrocarbons or aromatic organic groups; and (c) a conductive CNT film having a structure of substrate-[CONH—$R_2$—S-M-CNT-M-(S—$R_3$—S-M-CNT-M)p]q. Also, the present invention provides a method for fabricating the conductive CNT-biosensor.

In still another aspect, the present invention provides a method for detecting target biomaterials that bind to or react with bioreceptors, the method being characterized by using the conductive CNT-biosensor.

In yet another aspect, the present invention provides (i) a conductive CNT-M-nucleic acid complex wherein a nucleic acid is attached to the metal (M) of conductive CNTs having a form of CNT-(CONH—$R_1$—S-M)r, as well as (ii) a method for fabricating nucleic acid chips, which comprises attaching the nucleic acid complexes to a substrate having amine/lysine groups attached on its surface. In this inventive method, attaching the CNT-M-nucleic acid complexes to the substrate is preferably performed using cross-linking by UV irradiation, and the nucleic acid is preferably DNA.

In another aspect, the present invention provides DNA chips in which conductive CNT-Au-DNA complexes are attached to a solid substrate, as well as a method for detecting DNA hybridization reactions, which is characterized by using the DNA chips.

In still another aspect, the present invention provides CNT-M-enzymatic substrate complexes wherein an enzymatic substrate is attached to the metal (M) of conductive CNTs having a form of CNT-(CONH—$R_1$—S-M)r. In the complexes, the enzymatic substrate is preferably a kinase substrate peptide ($S^P$).

In another further aspect, the present invention provides a method for detecting kinase-involving enzymatic reactions, which is characterized by using the conductive CNT-M-$S^P$ complexes. In this inventive method, the detection of the enzymatic reactions is preferably performed using an electrical signal.

The target biomaterials that may be used in the broad practice of the present invention include substances capable of acting as targets that are detected by reaction or binding with bioreceptors, and such materials preferably include proteins, nucleic acids, antibodies, enzymes, carbohydrates, lipids, or other biomolecules derived from a living body, and more preferably disease-related proteins.

The bioreceptors as used in the present invention are preferably enzymatic substrates, ligands, amino acids, peptides, nucleic acids, lipids, cofactors, or carbohydrates, and also they preferably have thiol groups.

Although the metal as used in the present invention is preferably gold (Au), silver (Ag) nanoparticles, platinum (Pt) nanoparticles, iron (Fe) nanoparticles, nickel (Ni) nanoparticles, or cobalt (Co) nanoparticles, or any other suitable metal nanoparticles, may also be used in the present invention.

As used herein, the term "conductive CNT-biosensor" is defined to include biosensors where receptors that react with biomaterials are attached to the conductive CNTs, and this definition includes biochips attached to the conductive CNTs. Also, the term "dotting" means that the metal binds to CNTs in the form of dots, and the term "enzymatic substrates" is a general name for reaction materials involved in enzymatic reactions.

In the present invention, in order to improve the electrical properties of the existing CNTs, CNTs are dotted with metal nanoparticles. The CNTs dotted with the metal nanoparticles are repeatedly deposited on a solid substrate coated with chemical functional groups, by chemical binding, to fabricate a conductive CNT pattern (or film) having high surface density. Also, various bioreceptors having functional groups that react with the gold nanocrystals present in the high-density CNT pattern are attached to the CNT pattern or film, to fabricate a biosensor that can detect various target biomaterials directly or by electrochemical signals.

The present invention overcomes the limitations of the prior art methods in which CNTs were formed by growth from catalysts placed at certain locations, and allows the formation of the desired pattern on the desired locations at ambient temperature. In other words, methods for attaching CNTs to a substrate are broadly divisible into electrical methods and chemical methods. The electrical methods allow the locations of CNTs to be controlled in a relatively free manner, whereas the chemical methods adopt a process in which a substrate is modified with a certain functional group and then immersed in CNT suspension for a certain period of time. Thus, it is difficult for the chemical method to attach CNTs specifically only to the desired locations on the whole substrate.

To form various patterns by the binding of CNTs to the desired locations, the following requirements must be satisfied: (1) only certain portions of the substrate must be exposed, (2) they must be stable in CNT dispersion for a long period of time, and (3) they must be completely removed after the deposition of CNTs, such that an upper plate, formed of material such as PDMS, can be easily attached.

The present invention overcomes the drawbacks of the prior art by forming a substrate pattern using a polymer such that the advantages of the chemical methods can be utilized to the maximum possible extent. It is also possible to solve the problems of the prior art, including a difficulty in polymer patterning, caused by high-temperature mechanisms, such as plasma chemical vapor deposition and thermal chemical vapor deposition, and the absence of chemical functional groups, such as —COOH, which are obtained from a cutting process in a strong acid.

The use of the biosensor according to the present invention provides advantages in that exact values can be measured even with a small amount of reaction substances, and the concentration of ionic substances deposited on a surface can be electrically measured in a liquid phase.

Hereinafter, the present invention will be described in detail with reference to the accompanying drawings.

1. Production of CNTs Dotted with Gold Nanocrystals

FIG. 1 is a schematic diagram showing a method in which CNTs cut in a strong acid are dotted with gold particles by an oxidation-reduction method. The CNTs cut by a strong acid have a carboxyl (—COOH) functional group. The carboxyl functional group of the CNTs was bound to the amino functional group of a linker having both amino (—NH$_2$) and thiol (—SH) functional groups.

To accelerate the formation of the above amide bond HAMDU(O-(7-azabenzotriazol-1-yl)-1,3-dimethyl-1,3-dimethyleneuronium hexafluorophosphate), DCC(1,3-dicyclohexyl carbodiimide), HAPyU(O-(7-azabenzotriazol-1-yl)-1,1:3,3-bis(tetramethylene)uronium hexafluorophosphate), HATU(O-(7-azabenzotriazol-1-yl)-1,1:3,3-tetra methyluronium hexafluorophosphate), HBMDU (O-(benzotriazol-1-yl)-1,3-dimethyl-1,3-dimethyleneuronium hexafluorophosphate), or HBTU(O-(benzotriazol-1-yl)-1,1,3,3-tetramethyluronium hexafluorophosphate) is preferably used as a coupling agent, and DIEA(diisopropylethylamine), TMP(2,4,6-trimethylpyridine), or NMI(N-methylimidazole) is preferably used as a base.

Also, in the case of using water as solvent, EDC(1-ethyl-3-(3-dimethylamini-propyl)arbodiimide hydrochloride) is preferably used as a coupling agent, and NHS(N-hydroxysuccinimide) or NHSS(N-hydroxysulfosuccinimide) is preferably used as a co-coupling agent (base).

The linker having both amino and thiol functional groups is preferably a chemical substance of the formula NH$_2$—R$_1$—SH wherein R$_1$ represents C$_{1-20}$ saturated hydrocarbons, unsaturated hydrocarbons, or aromatic organic groups, e.g., methylene, ethylene, propylene, pentamethylene, phenylene, pentenylene, etc.

The CNTs modified with the thiol functional group were reacted with gold nanoparticles, such as HAuCl$_4$, HAuCl$_4$.3H$_2$O, HAuBr$_4$, AuCl$_4$K, AuCl$_4$Na, AuBr$_4$K, and AuBr$_4$Na, and preferably HAuCl$_4$ gold colloids, to produce gold nucleation sites, and then, the gold nanoparticles were reduced by ion extraction reaction as shown in the following reaction scheme 1, to dot the CNTs with gold crystals.

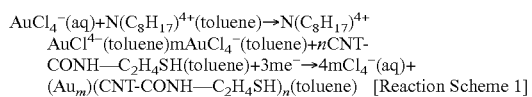

AuCl$_4^-$(aq)+N(C$_8$H$_{17}$)$^{4+}$(toluene)→N(C$_8$H$_{17}$)$^{4+}$
AuCl$^{4-}$(toluene)mAuCl$_4^-$(toluene)+nCNT-
CONH—C$_2$H$_4$SH(toluene)+3me$^-$→4mCl$_4^-$(aq)+
(Au$_m$)(CNT-CONH—C$_2$H$_4$SH)$_n$(toluene)  [Reaction Scheme 1]

Finally, the gold-dotted conductive CNTs having a form of CNT-(CONH—R$_1$—S—Au)r wherein r is a natural number greater than 1 was obtained.

As a substitute for gold, silver (Ag) nanoparticles, platinum (Pt) nanoparticles, iron (Fe) nanoparticles, nickel (Ni) nanoparticles, cobalt (Co) nanoparticles, etc., may also be used. The metal particles in an oxidized state can be dotted on CNTs modified with a specific chemical functional group, such as a thiol functional group, by reducing the metal using oxidation-reduction reaction (Jiang, K. et al., *Nano Lett.*, 3:275, 2003).

2. Formation of Multichannel-Type Pattern on Substrate

In order to immobilize CNTs on the desired locations of a substrate, such as glass, a silicon wafer or plastic, a pattern which can be stable in a liquid phase needs to be formed. Methods for forming the pattern on the substrate are divided into two methods. The first method is the one wherein portions of the substrate to be deposited with CNTs are removed using a negative photoresist, CNTs are deposited on the substrate, and the remaining photoresist is removed. The second method is the one wherein portions of a polymer substrate to be deposited with CNTs are etched by photolithography.

In a specific process, as the first method using the negative photoresist, the most general method for semiconductor fabrication can be used which comprises covering a substrate with a photoresist film, such as SU-8 (Dowcorning Co.), removing only the desired portions of the substrate by a photolithographic process, depositing CNTs on the removed portions of the substrate, and removing the remaining photoresist film.

As shown in FIGS. 2a to 2d, the second method comprises providing a silicon substrate (FIG. 2a), spin-coating a photoresist film on the substrate (FIG. 2b), exposing the resulting substrate to light through a mask having a given shape (FIG. 2c), and developing the exposed photoresist pattern (FIG. 2d), thereby forming a first pattern on the silicon substrate by a photolithographic process. Next, a liquid polymer is poured on the resulting substrate and semi-cured at 50° C. for about one hour (FIG. 2e), and an additional photolithographic process is conducted on the semi-cured semi-liquid polymer (FIG. 2f). As shown in FIG. 2g, the desired portions of the polymer from which the photoresist film was removed are removed by etching with piranha solution (sulfuric acid:nitric acid=3:1) or aqua regia (sulfuric acid:hydrogen peroxide=10:1), etc., and then, as shown in FIG. 2h, the remaining photoresist film is removed.

The resulting semi-cured polymer is completely cured at 70° C. for two hours. The cured polymer is detached from the silicon substrate, and hydrophilic groups are formed on the surface of the detached polymer film by corona discharge. When the polymer film with the hydrophilic groups is attached on a clean silicon substrate, only the desired portions of the silicon substrate are exposed, such that CNTs can be chemically deposited only on the desired portions of the substrate.

As described above, forming the desired pattern on the substrate is most important in forming the CNT pattern. Other methods include a method comprising placing a stamp having a given shape on a silicon substrate, pouring a liquid polymer on the substrate with the stamp, and curing the poured polymer. More macroscopically, only the desired portions of the cured polymer film can be physically removed, thereby forming a polymer mask.

In the existing biochips with CNTs, CNTs were grown on certain locations of a substrate and used to provide electrical and optical measurement results, but the present invention has an advantage in that it allows CNTs to be attached or deposited on the desired locations of a substrate.

Figure 6:
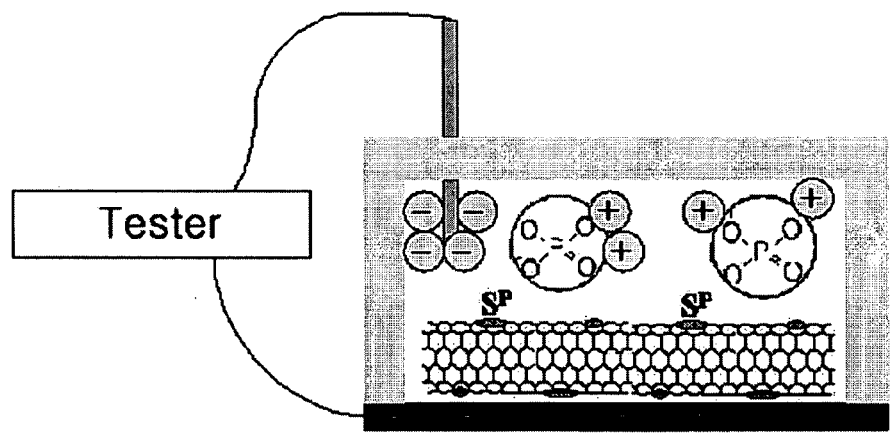
FIG. 6 is a schematic diagram showing ions produced by kinase enzyme reaction using a substrate peptide immobilized on CNTs being measured by inducing oxidation-reduction reaction.
Figure 7:
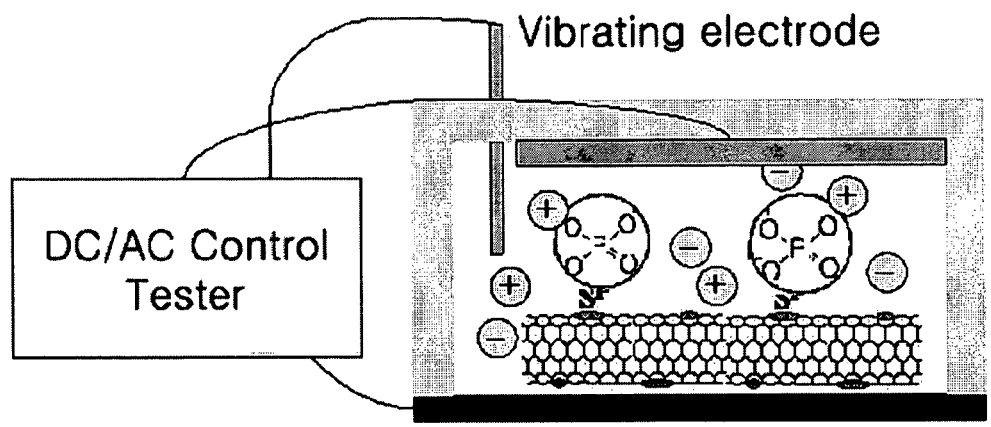
FIG. 7 is a schematic diagram showing the concentration of ions produced by kinase enzyme reaction using a substrate peptide immobilized on CNTs being measured using a capacitor.
Figure 8:
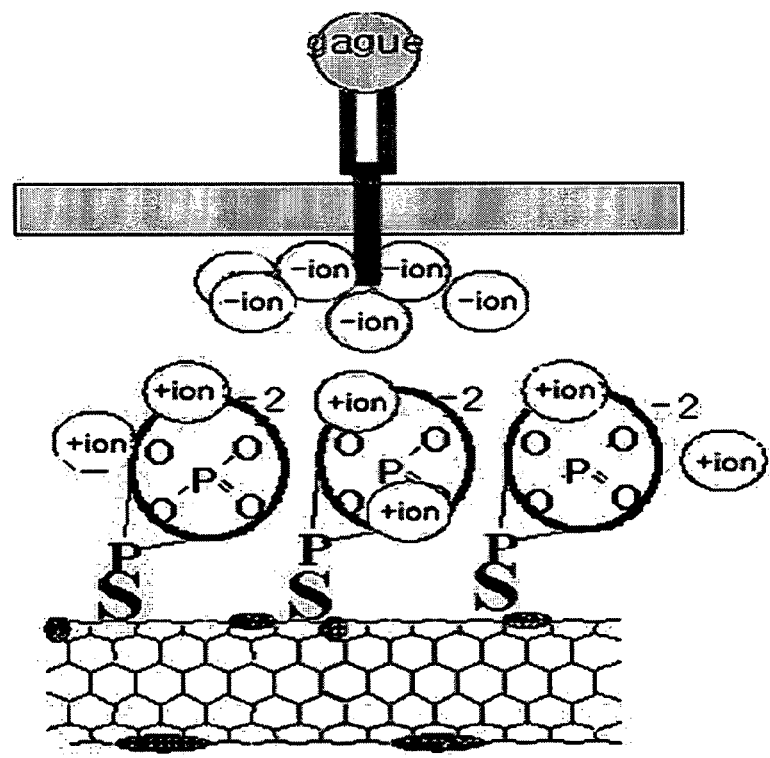
FIG. 8 is a schematic diagram showing the concentration of ions produced by kinase enzyme reaction using a substrate peptide immobilized on CNTs being measured by using a charged plate inserted into a polymer chip.

As described above, in order to electrically detect biomaterials attached to a substrate having CNTs arranged thereon, the biomaterials must be maintained in a liquid state as shown in FIGS. 6 to 8, and an upper plate required in this detection must have several mm-several μm of secured space in which fluid will be contained. The substrate which can be used in this detection may be formed of various polymer materials, such as polydimethylsiloxane (PDMS), polymethylmethacrylate (PMMA), polycarbonate (PC), polyethylene (PE), polypropylene (PP), and polystyrene (PS).

According to the present invention, an electric power source can be connected through at least one conductive nanowire so that charge can be applied to each liquid phase comprising the target biomaterials placed on the CNT or CNT chip, in which the conductive nanowire can be formed as a single atom according to conventional technology (Kouwenhoven, L., *Science*, 275:1896, 1997), by forming a predetermined pattern on a conductive metal and depositing a wire, through which an electric current can flow, by ion implantation or sputtering.

3. Production of Thiol (—SH) Functional Groups on Solid Substrate

In the present invention, a method is used which comprises forming a photoresist or polymer pattern on a substrate, such as glass, a silicon wafer or plastic, and then immobilizing aminoalkyloxysilane on the substrate surface using the pattern as a mask, to expose an amino group to the substrate surface. As the aminoalkyloxysilane, aminopropyltriethoxysilane is preferably used.

To expose a thiol functional group to the substrate surface having the amino group immobilized thereto, an amide bond is formed by the reaction between the amino group on the substrate and the carboxyl functional group of a chemical substance having both thiol and carboxyl groups, such as HOOC—$R_2$—SH wherein $R_2$ represents $C_{1-20}$ saturated hydrocarbons, unsaturated hydrocarbons or aromatic organic groups. Ultimately, a structure in the form of substrate-CONH—$R_2$—SH having exposed thiol group functionality is formed.

Figure 3A:
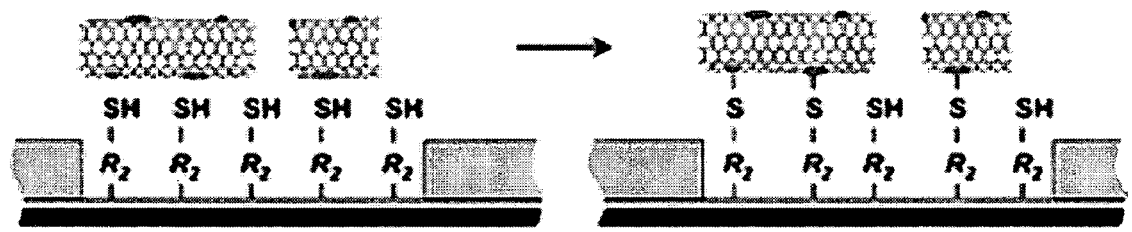
FIG. 3a is a schematic diagram showing that a thiol (—SH) group is exposed to a substrate surface having a pattern formed thereon, and a CNT monolayer dotted with gold nanocrystals is immobilized to the substrate surface.

In the reaction to form the amide bond, a substance selected from the group consisting of DCC, HATU, HBTU, HAPyU, HAMDU and HBMDU is preferably used as a coupling agent, and a substance selected from the group consisting of DIEA, TMP and NMI is preferably used as a base. Also in the case of using water as a solvent, EDC is preferably used as a coupling agent, and NHS or NHSS is preferably used as a co-coupling agent 4. Method for Forming Pattern or Film by Deposition of CNTs on Substrate First, CNTs dotted with gold (Au-CNT-Au) are bound to a substrate having a thiol functional group exposed to its surface (substrate-CONH—$R_2$—SH). At this time, an Au—S bond is formed between the thiol functional group on the substrate surface and the gold crystal of the gold-dotted CNTs, so that the CNTs are bound on the substrate, thereby forming a structure in the form of substrate-CONH—$R_2$—S—Au-CNT-Au (FIG. 3a).

Figure 3B:
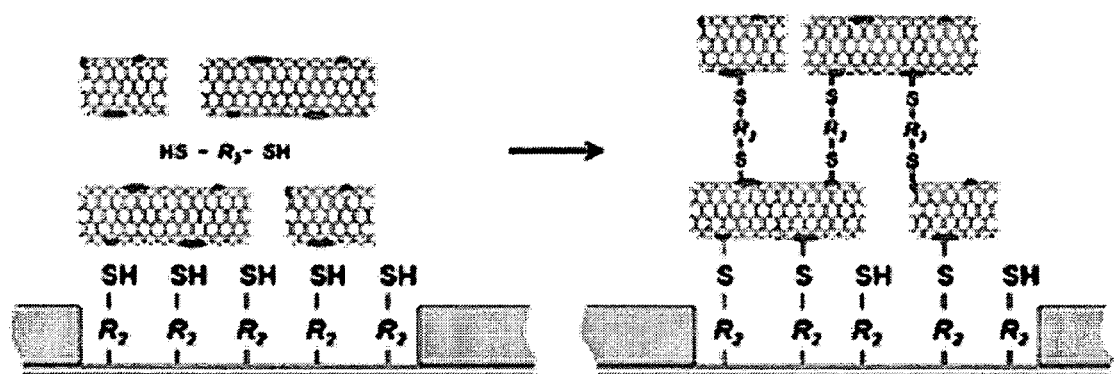
FIG. 3b is a schematic diagram showing other CNTs dotted with gold nanocrystals immobilized to the CNT monolayer of FIG. 3a by a chemical substance having two thiol groups.

Thereafter, the gold of the gold-dotted CNTs which were selectively attached to the substrate is reacted with one thiol group of a chemical substance represented by HS—$R_3$—SH, which is a linker having thiol functional groups, and the gold-dotted CNTs are reacted with the other thiol group of the linker. By such reactions, a structure in the form of substrate-[CONH—$R_2$—S—Au-CNT-Au-S—$R_3$—S—Au-CNT-Au] is formed (FIG. 3b).

Figure 3C:
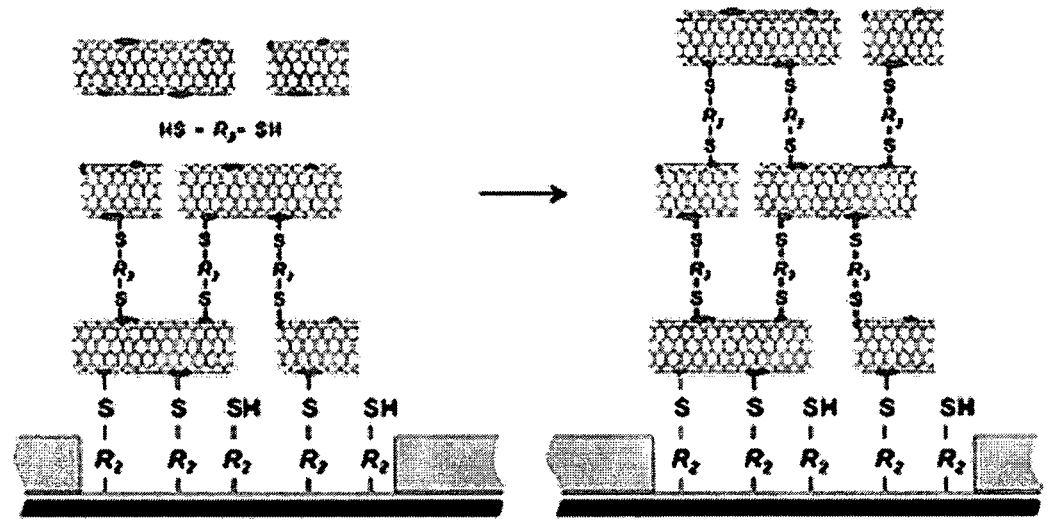
FIG. 3c is a schematic diagram showing a method for increasing the surface density of gold nanoparticle-dotted CNT by repeating the method of FIG. 3b.
Figure 3D:
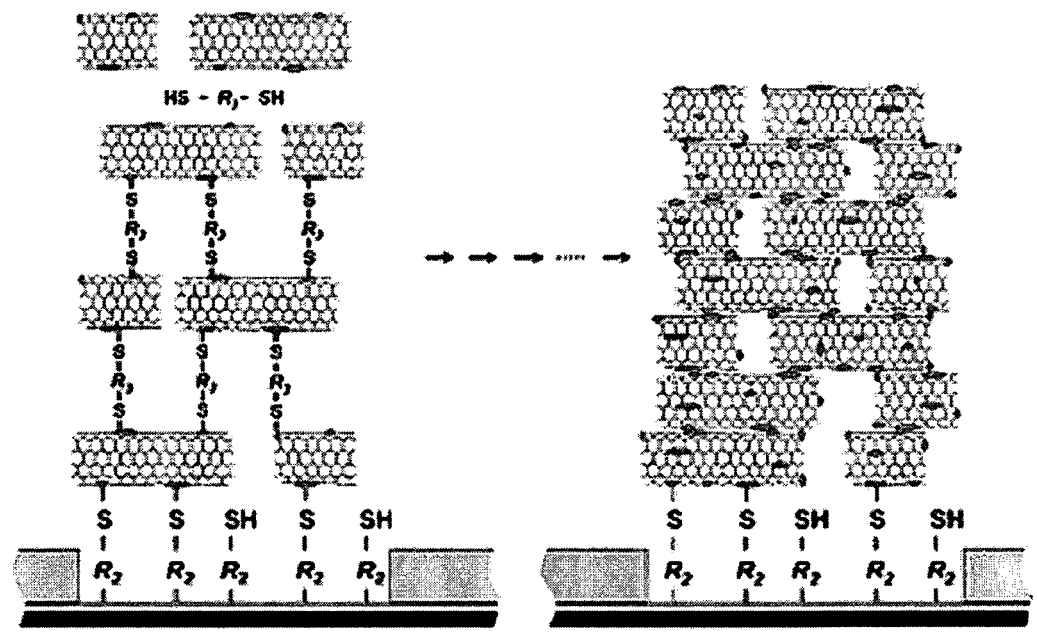
FIG. 3d is a schematic diagram showing a method for depositing gold nanoparticle-dotted CNTs to high density, by repeating the method of FIG. 3c.
Figure 3E:
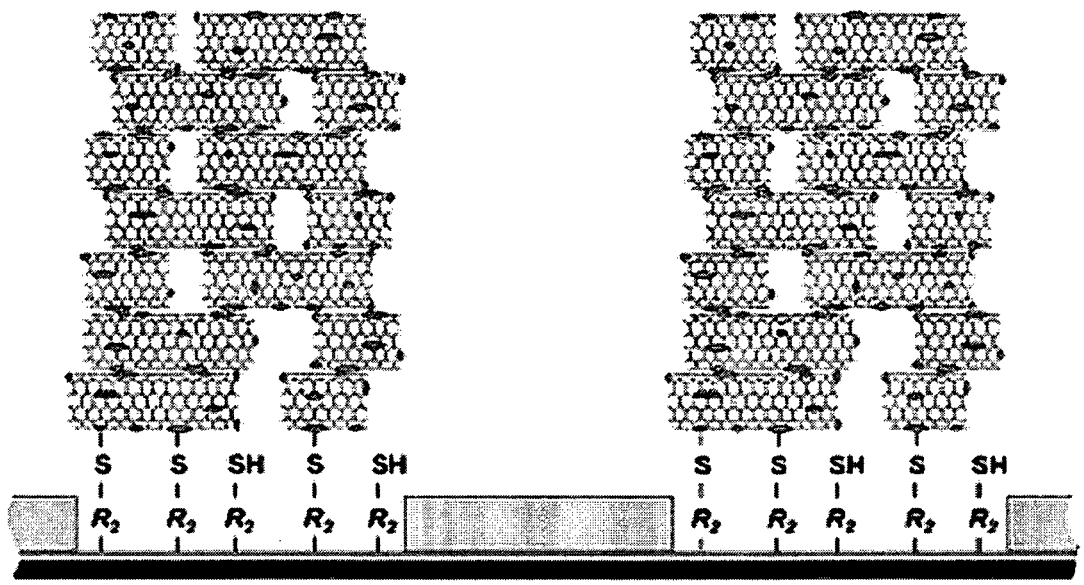
FIG. 3e is a schematic diagram showing CNTs dotted with gold nanoparticles deposited on the substrate at high density to form a CNT pattern.

Following this, the chemical reaction between the gold-dotted CNTs and the chemical substance having double thiol functional groups is repeatedly carried out to increase the surface density of the conductive CNT on the substrate surface. Ultimately, this yields a conductive CNT pattern or film having a structure of substrate-[CONH—$R_2$—S—Au-CNT-Au-(S—$R_3$—S—Au-CNT-Au)p]q' wherein p and q are natural numbers greater than 1 (FIGS. 3c to 3e).

5. Method for Binding Receptors to Conductive CNTs Dotted with Gold

In the present invention, bioreceptors are substances that bind to or react with target biomaterials, and they are preferably substances serving as probes capable of detecting this binding or reaction. Examples of such bioreceptors include nucleic acids, proteins, peptides, amino acids, ligands, enzyme substrates, and cofactors. The target biomaterials as used in the present invention are substances capable of acting as targets by binding or reacting with the bioreceptors, and their examples include proteins, nucleic acids, enzymes, and other biomolecules.

Figure 4:
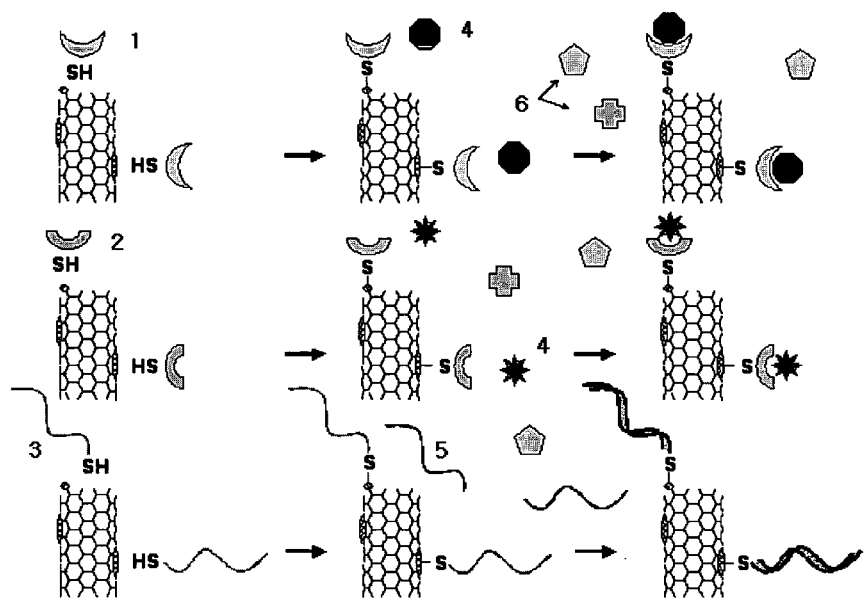
FIG. 4 is a schematic diagram showing that various receptors having functional groups that bind to or react with the gold nanoparticles of gold nanoparticle-dotted CNTs are attached and then selectively interacted with various target biomaterials. Reference numerals 1 and 2 denote bioreceptors capable of reacting with target biomaterials, reference numeral 4 denotes target biomaterials capable of reacting with the bioreceptors, and reference numeral 3 denotes oligonucleotides among the bioreceptors. Reference numeral 5 denotes complementary nucleic acids capable of hybridizing with the oligonucleotides immobilized to the metal of conductive CNTs, and reference numeral 6 denotes general biomaterials having no reactivity.

FIG. 4 is a schematic diagram showing that various bioreceptors having functional groups that bind to or react with gold are attached to the surface of CNTs dotted with gold nanoparticles, and then selectively interacted with various target biomaterials. As the functional groups that react with the gold nanocrystals, thiol groups are preferably included. In FIG. 4, reference numerals 1 and 2 denote bioreceptors capable of reacting with target biomaterials, and reference numeral 4 denotes target biomaterials capable of reacting with the bioreceptors. Also, reference numeral 3 denotes oligonucleotides among the bioreceptors, reference numeral 5 denotes complementary nucleic acids capable of hybridizing with the oligonucleotides immobilized to the metal of conductive CNTs, and reference numeral 6 denotes general biomaterials having no reactivity.

Figure 5:
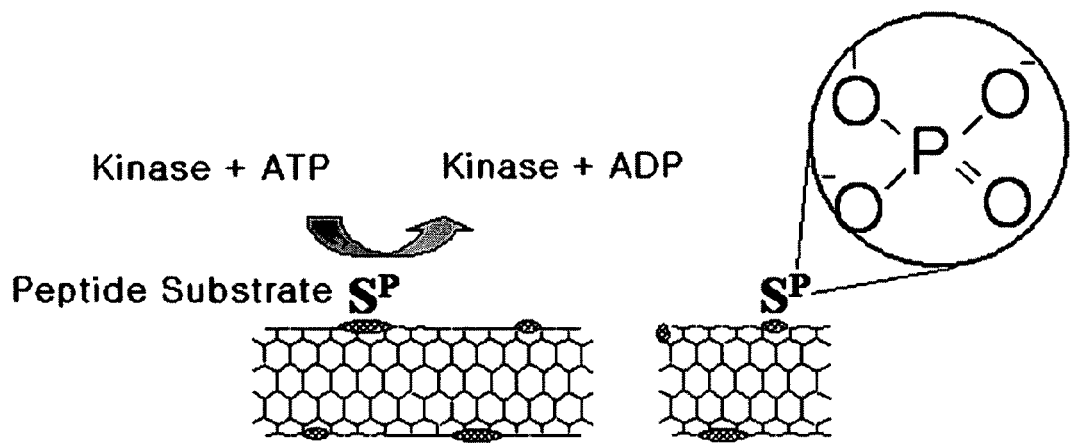
FIG. 5 shows a CNT-Au-substrate peptide complex where a kinase substrate peptide having a thiol functional group is immobilized to CNTs dotted with gold nanoparticles, for kinase enzyme reaction.

FIG. 5 shows a CNT-Au-substrate peptide complex where substrate peptide ($S^P$) of a kinase having thiol functional group is immobilized to CNTs dotted with gold nanoparticles, for kinase enzyme reaction. The application of this complex in phosphorylation by various kinase enzymes allows the measurement of electrochemical change of CNTs.

Methods that can be used to detect the reaction between the bioreceptors and the biomaterials include, without limitation, an electrical detection method well known as the intrusion detection system in the art, a resonance method, and method using a fluorescent body. The electrical detection method using electrical signals is preferably used, in which case a minute change in potential difference, which occurs in CNTs during the reaction between bioreceptors and biomaterials, can be monitored through a suitable circuit.

6. Reaction Detection System

The use of a probe station for the measurement of electrical properties of biosensors and a fluorescent microscope for the detection of fluorescent substances generated in the biosensors allows the measurement of reactions. Moreover, the existing method may also be used which comprises attaching a radioisotope to reaction substances, reacting the resulting substances, and then measuring radiation on a given surface using a radiation meter.

For the utilization of the sensitive electrical properties of CNTs, the electrical detection method among the above methods was embodied in the present invention. Since the measurement of reactions is mainly performed in a liquid state due to the characteristics of biomaterials, the present invention focused on measuring the electrical values of CNTs in a liquid state. To measure the ionic concentration of biomaterials attached to the surface of CNTs, three methods were used. If the CNT-Au-substrate peptide complex where the substrate peptide of a kinase enzyme is bound to the surface of CNTs as shown in FIG. 5 is applied to kinase enzyme reaction, the ionic concentrations of biomaterials resulting from the kinase enzyme reaction can be measured by the following three methods.

The first method is to measure oxidation-reduction reaction with equipment, such as a potentiostat, after inducing the reaction by a special solute. The second method is to use the concept of a capacitor to measure the concentration of ions in a capacitor plate by electrical control. The third method is to use the principle of a charged body to measure the extent to which the charged thin films of a charged plate are widened, according to the intensity of the surrounding ions.

The oxidation-reduction reaction of the first method is an electrochemical detection method which is currently generally used. As shown in FIG. 6, electrodes are immersed in a special solute-containing liquid covering the conductive lines and biomaterials connected to CNTs, and the results before and after reaction are measured with a Potentiostat/Galvanostat (Ametech Co.) using cyclic voltammetry, potentiometry and amperometry.

As shown in FIG. 7, in the measurement of ionic concentrations using the principle of capacitors according to the second method, a new substrate formed of platinum or gold is disposed on a CNT-attached substrate with liquid interposing therebetween, and is connected with electrodes. Vibrations produced in the solution can be measured by immersing a vibrating electrode in an electrolyte-containing solution and suitably applying a direct current and an alternating current.

As shown in FIG. 8, the third method using the principle of a charged plate comprises inserting a charged plate into a chip covered with polymer, and measuring the extent to which the charged thin films of the charged plate are widened, with a gauge.

In this case, the correlation between an electrolyte and an electric current is expressed as "the concentration of electrolyte aqueous solution ∝ the intensity of an electric current". In other words, since the concentration distribution of an electrolyte according to the ionic concentration of reaction materials produced on the surface of CNTs is in proportion to the intensity of an electric current, the concentration of ions formed in the underside mechanism can be measured.

EXAMPLES

The present invention will hereinafter be described in further detail by examples. It will however be obvious to a person skilled in the art that these examples are presented to the present invention in more detail, and the scope of the present invention is not limited to or by the examples.

Example 1

Production of CNTs Dotted with Gold (Au)

Single walled carbon nanotubes (SWNTs) were cut with a strong acid and then the resulting CNTs having carboxyl functional groups were subjected to oxidation-reduction reaction in a two-phase liquid-liquid system, to produce CNTs dotted with gold nanoparticles (FIG. 1).

First, by aid of a coupling agent (DCC) in an ethanol solvent, a linker (2-aminoethanethiol) having both amino (—$NH_2$) and thiol (—SH) functional groups was stirred with the CNTs having carboxyl functional groups at ambient temperature for about 24 hours. Gold nucleation sites were formed at the binding locations on the end and side of the CNTs by Au-S chemical bonds.

25 ml of 0.01% gold colloidal solution that is light yellow in color was charged into a glass reactor, to which a solution of 16.5 ml (0.01665 mmol) of $N(C_8H_{17})_4Br$ in toluene was then added slowly while stirring the gold colloidal solution rapidly. In this reaction, a phase separation between water and toluene occurred, and the mixed solution was very rapidly stirred until the color of the lower aqueous layer completely disappeared. 2 mg of the CNTs having the thiol groups formed thereon was dispersed in 10 ml of toluene, and added slowly to the upper toluene layer (organic phase). Then, a solution of 20.5 ml (0.0825 mmol) of $NaBH_4$ in water was added with slow stirring. This reaction mixture was stirred rapidly at ambient temperature for 20 hours, after which the toluene organic phase was separated from the aqueous phase by a separatory funnel. The separated organic phase was filtered through a polyvinylidenefluoride (PVDF) membrane filter having a pore size of 100 nm, during which toluene and ethanol were added several times.

The filtered sample was placed in triple-distilled water, and dispersed by ultrasonic waves. The dispersion was centrifuged at 2,000 rpm for 60 minutes. After removing the supernatant, the sample was filtered through a membrane filter again, and the resulting sample was dried in vacuum.

The gold crystal-dotted CNT produced by the above method was analyzed by a transmission electron microscope (TEM) and an X-ray photoelectron spectroscope (XPS). FIG. 9a is a TEM photograph showing the gold nanocrystal-dotted CNT obtained by forming thiol (—SH) groups on a CNT and reacting the formed thiol groups with gold colloids, and FIG. 9b is a TEM photograph showing a CNT obtained by reacting a CNT having no thiol (—SH) groups formed thereon with gold colloids. From these photographs, it is determined that the gold crystals formed on the CNT having thiol groups were dotted at a larger number on the side of the CNT than on the ends thereof, and they were not dotted on the CNT having no thiol groups.

Figure 9:
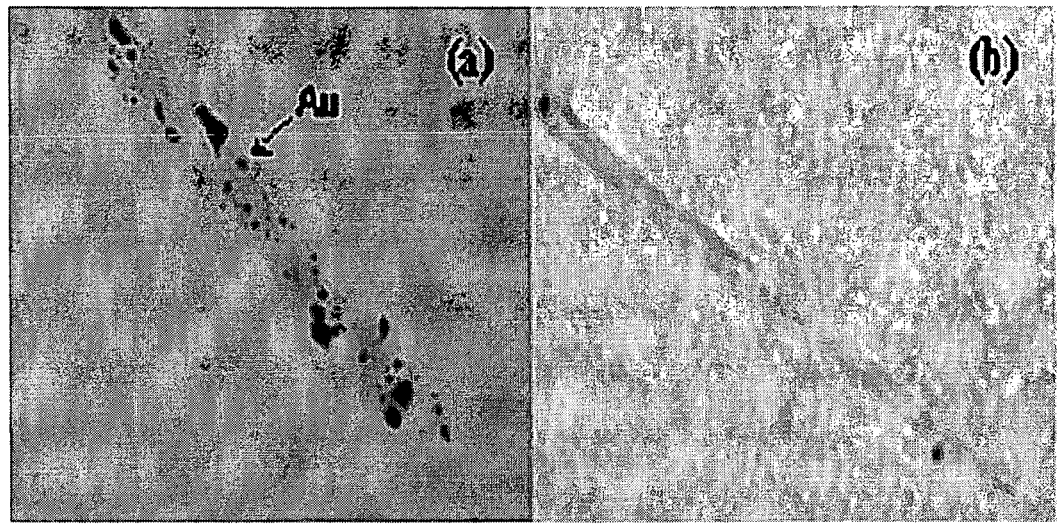
FIG. 9a is a TEM photograph showing a gold crystal-dotted CNT obtained by forming thiol (—SH) groups on a CNT and reacting the thiol groups with gold colloids.
FIG. 9b is a TEM photograph showing a CNT obtained by reacting gold colloids with a CNT having no thiol (—SH) groups.
Figure 10:
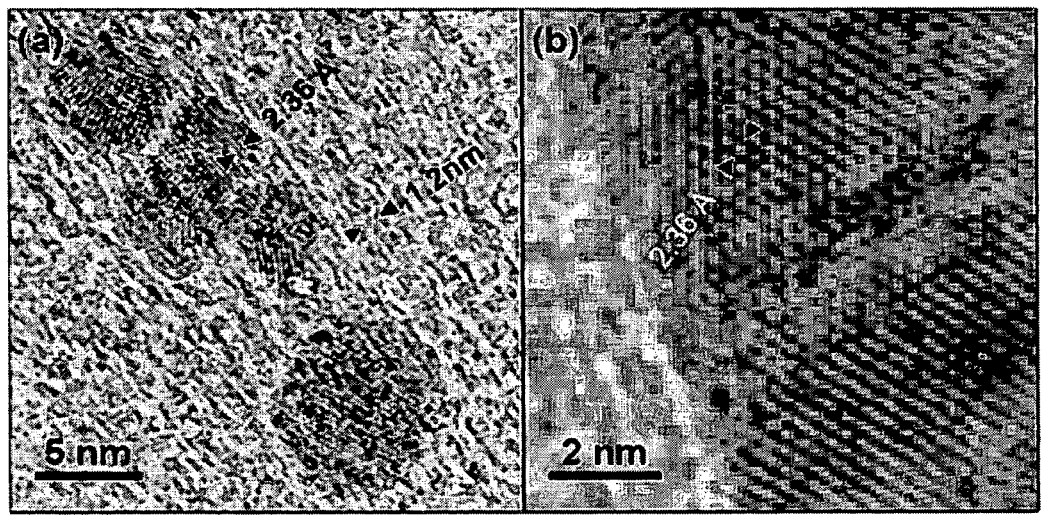
FIG. 10 is a HR-TEM photograph of FIG. 9 enlarged to high magnification.

FIG. 10 is a HR-TEM photograph showing the CNT of FIG. 9 enlarged to high magnification. The regular d-spacing of lattices measured in this photograph was 2.36±0.02 Å. This value is nearly equal to the value in the literature for the {111} plane of gold (2.355 Å) (Powder Diffraction Data File 38-1364, Inorganic Phases, JCPDS International Centre for Diffraction Data, Swathmore, Pa., 199).

Figure 11:
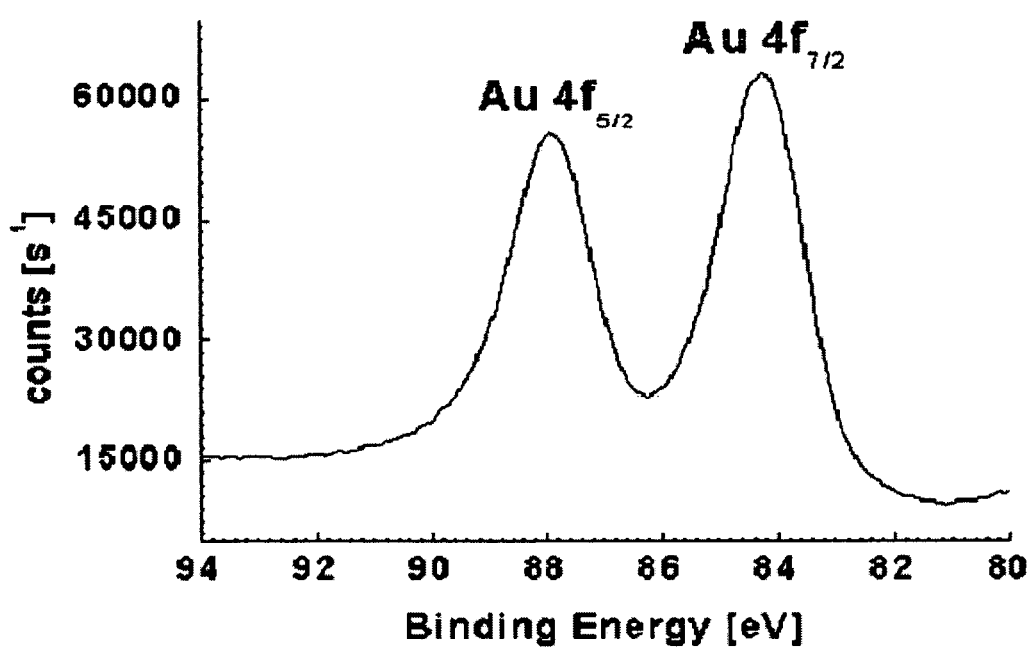
FIG. 11 is an XPS doublet spectrum for gold crystals dotted on CNTs.

The oxidation state of gold crystals dotted on the CNT can also be examined by XPS. FIG. 11 shows an XPS doublet spectrum for gold crystals dotted on the CNT. The doublet binding energies of gold (Au) are Au $4f_{5/2}$(87.9 eV) and Au $4f_{7/2}$(84.2 eV), respectively. These values correspond to those of gold in a reduction state ($Au^0$). This suggests that most of the gold crystals dotted on the CNT surface are in a reduction state other than a colloidal state.

Example 2

Detection of DNA Hybridization Reaction Using CNT Dotted with Gold

Figure 12A:
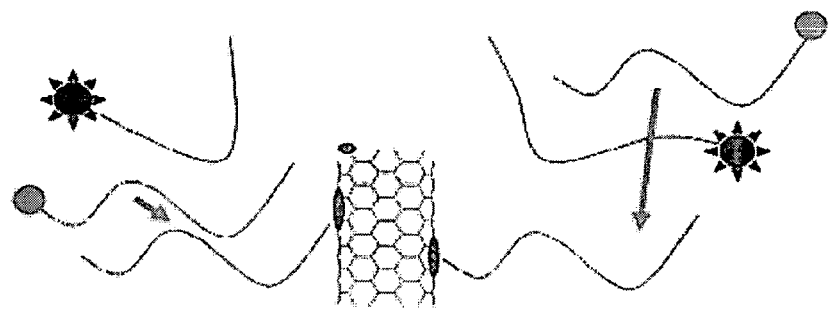
FIG. 12a shows that DNA is specifically bound to gold nanoparticles dotted on the wall surface of a CNT.

Thiol group-containing DNAs or oligonucleotides bind specifically to gold nanocrystals dotted on the wall surface of a CNT, to form a CNT-Au-DNA complex (FIG. 12a). The oligonucleotide-bound CNT was immobilized on a glass slide (Shin-Won Scientific Co. Ltd., Korea) treated with poly-L-lysine, in the same manner as in the fabrication of DNA chips (Schena, M. et al., *Science* 270:467, 1995).

The oligonucleotide-bound CNT of the following SEQ ID NO: 1 was filtered several times through a 0.2 µm Teflon filter to remove unreacted oligonucleotides. After the filtration, the oligonucleotide-bound CNT solution was concentrated with a centrifuge.

5'-TGT GCC ACC TAC AAG CTG TG (C3)-thiol-3 (SEQ ID NO: 1)

10 µl of the concentrated oligonucleotides were dropped onto the glass substrate treated with poly-L-lysine by a pipette, and then dried at ambient temperature for at least 12 hours. Next, the resulting substrate was placed into a damp chamber containing 1×SSC (0.15M NaCl 0.015M sodium citrate) and left until the dried substance on the glass substrate twinkled by saturation (for about one minute). Thereafter, it was placed into a 95° C. oven, allowed to react for 3 seconds, and then immobilized using an UV crosslinker system (Spectrolinker XL-1500 UV crosslinker) at 650 mJ.

Figure 12B:
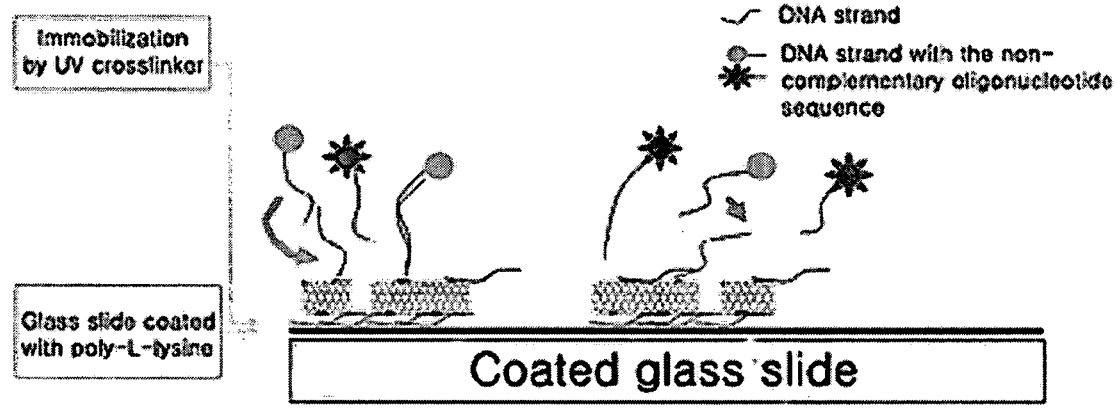
FIG. 12b shows that a CNT-Au-DNA complex is bound to the surface of a substrate.

The negative phosphate group ($PO^{4-}$) of oligonucleotides binds electrostatically to the positive amino group ($NH^{3+}$) of poly-L-lysine. If they are irradiated with ultraviolet rays and dried in a hot oven for about 3 seconds, a covalent bond is then formed to immobilize the CNT onto the glass substrate by the oligomer as a linker. FIG. 12b shows that CNT-Au-DNA complexes are bound to the surface of the glass substrate treated with poly-L-lysine.

To block unreacted amino groups on a glass slide (Corning cop.) whose surface was treated with amino groups, 6 g of succinic anhydride (Sigma) was dissolved in 350 ml of 1-methyl-2-pyrrolidinone (Sigma). After the succinic anhydride was completely dissolved, 15 ml of 1M sodium borate (pH 8.0) was added and the glass slide was immersed therein for 15 minutes. At this time, the succinic anhydride is attached to the amino groups on the glass slide to play a blocking role.

Thereafter, to remove an excess of solvent, the resulting glass slide was immersed in ultrapure water at 95° C. for 1 minute, allowed to react in ethanol for 2 minutes, centrifuged at 600 rpm and then dried.

The chip prepared as described above was placed in a mixture solution of 3.5×SSC (0.525M NaCl, 0.0525M sodium citrate, pH 7.0), 0.1% SDS, and 10 mg/mL bovine serum albumin (BSA), allowed to react at 50° C. for 20 minutes, immersed two times in ultrapure distilled water for one minute each time, and then immersed in isopropyl alcohol for one minute. Thereafter, centrifugation was performed at 600 rpm for 5 minutes to remove an excess of solution remaining on the chip.

The DNA chip prepared was placed in a hybridization chamber and a hybridization solution was dropped at where the CNT had been fixed using a pipette. Then, a cover slide was placed thereon. Here, the hybridization solution was prepared with 32 µl of a solution containing an oligonucleotide of complementary sequence to be a total volume of 40 µl at a final concentration of 3×SSC (0.45M NaCl, 0.045M sodium citrate) and 0.3% SDS(sodium dodecyl sulfate). The complementary oligonucleotide sequence was the following SEQ ID NO 2 having FITC (fluorescein isothiocyanate) attached to its end.

5'-CAC AGC TTG TAG GTG GCA CA FITC 3' (SEQ ID NO: 2)

To remove the non-specific bindings of the double-stranded oligonucleotides, the solution was left at 100° C. for 2 minutes, followed by centrifugation at 12,000 rpm for 2 minutes. In order to prevent the hybridization solution from being dried in the hybridization chamber, each 30 µl of 3×SSC (0.45M NaCl, 0.045M sodium citrate) was placed into each of the recesses at both edges of the hybridization chamber. The chamber was covered with a lid and left to stand in a constant temperature bath at 55° C. for 10 hours.

After 10 hours, the hybridization chamber was taken out from the constant temperature bath, immersed in 2×SSC solution for 2 minutes, and then immersed in a mixed solution of 0.1×SSC (0.015M NaCl, 0.0015M sodium citrate) and 0.1% SDS for 5 minutes, and finally in 0.1×SSC for 5 minutes. To remove the solution remaining on the chip, the chip was placed in a centrifuge and centrifuged at 600 rpm for 5 minutes.

The fluorescent image was obtained using ScanArray 5000 (Packard BioScience, BioChip Tecnologies LLC) confocal microscope and the QuantArray Microarray Analysis Software.

Figure 13A:
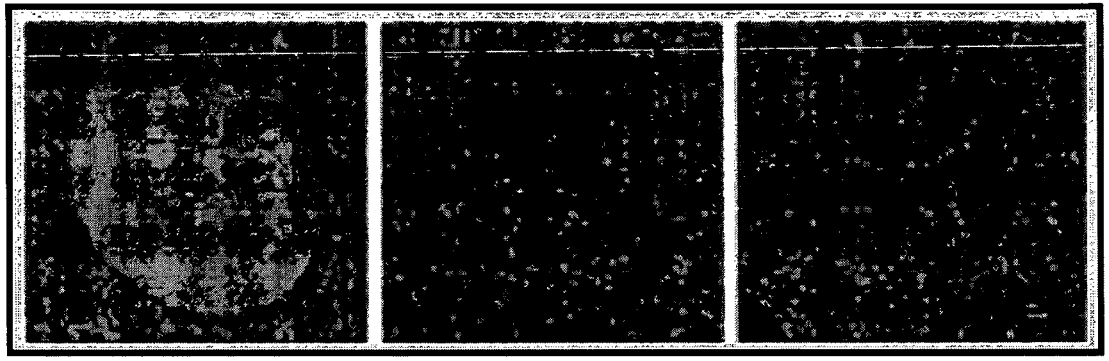
FIG. 13a is a photograph showing the comparison of the results of interaction between various DNAs and CNTs.

It was confirmed that the fluorescence was clear and even when the oligonucleotide having the sequence complementary to the CNT-DNA chip was hybridized (left side of FIG. 13(a)). However, in the CNT pattern without the oligonucleotide fixed thereon and in the CNT-DNA chip hybridized with the oligonucleotide having the non-complementary sequence, no fluorescence was observed (center and right side of FIG. 13(a)). From these results, it was confirmed that the non-specific reaction almost never occurred.

Figure 13B:
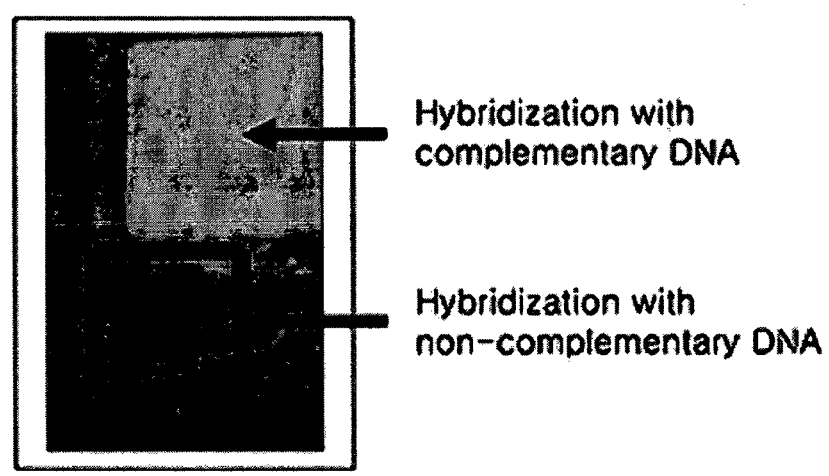
FIG. 13b is a photograph showing the results of comparison to determine if DNA complementarily binds to a CNT pattern.

Also, as shown in FIG. 13(b), oligonucleotide was attached on a glass substrate coated with CNT and then, oligonucleotide having non-complementary sequence and oligonucleotide having complementary sequence was hybridized. As a result, it was possible to accurately distinguish between the hybridized sample and the non-hybridized sample.

As described in detail above, the present invention provides metal-dotted conductive CNTs having much higher electrical conductivity than that of the existing CNTs, as well as a pattern or film of the conductive CNTs. Furthermore, the present invention provides the biosensor wherein bioreceptors that react with biomaterials are attached to the conductive CNT pattern or film.

The conductive CNT-biosensor according to the present invention has a large surface area and excellent electrical conductivity properties, making it possible to increase the immobilized amount of biomolecules, such as DNA, and to improve the detection sensitivity to the biomolecules. Moreover, by detecting various target biomolecules directly or measuring electrochemical signals, it can precisely detect the reactions between biomaterials and bioreceptors at large amounts in one step.

Also, the inventive biosensor meets the requirement that biomaterials must be mainly measured with a small amount of samples in a liquid state due to their characteristics. In addition, it is possible for the inventive biosensor to accommodate an electrical detection method capable of providing precise measurement results.

What is claimed is:

1. A conductive carbon nanotube (CNT)-biosensor comprising a bioreceptor that binds to or reacts with target biomaterials attached to (i) a conductive CNT pattern, having a structure of substrate-[CONH—$R_2$—S-M-CNT-M-(S—$R_3$—S-M-CNT-M)p]q or (ii) a conductive carbon nanotube (CNT) film, having a structure of substrate-[CONH—$R_2$—S-M-CNT-M-(S—$R_3$—S-M-CNT-M)p]q; wherein M represents a metal dotted on the CNT, p and q are natural numbers greater than 1, and $R_2$ and $R_3$ are each independently selected from $C_{1-20}$ saturated hydrocarbons and unsaturated hydrocarbons.

2. The conductive CNT-biosensor according to claim 1, wherein the bioreceptor is an enzymatic substrate, a ligand, an amino acid, a peptides, a nucleic acid, a lipid, a cofactor, or a carbohydrate.

3. The conductive CNT-biosensor according to claim 1, wherein the bioreceptor has thiol groups.

4. The conductive CNT-biosensor according to claim 1, wherein the metal is gold (Au).

5. A method for detecting a target biomaterial that binds to or reacts with a bioreceptor, the method comprising contacting the target biomaterial with the conductive CNT-biosensor of claim 1 and detecting target biomaterial that has bound to or reacted with the bioreceptor.

6. The method according to claim 5, wherein the detection is performed by using an electrical signal.

7. The conductive CNT biosensor according to claim 1, wherein the CNT pattern is prepared by the method comprising the steps of: (a) providing a substrate having thiol groups exposed on its surface in a form of pattern; (b) binding a metal of conductive CNTs dotted with the metal to the thiol groups on the substrate surface, wherein said conductive CNT dotted with the metal has a form of CNT-(CONH—$R_1$—S-M)r; (c) binding conductive CNTs to the bound conductive CNTs, to deposit the conductive CNTs; and (d) repeating the step (c), wherein M represents a metal, r is a natural number greater than 1, and $R_1$ is selected from $C_{1-20}$ saturated hydrocarbons and unsaturated hydrocarbons.

8. The conductive CNT biosensor according to claim 1, wherein the CNT pattern is prepared by the method comprising the steps of: (a) providing a substrate having thiol groups exposed to its surface; (b) binding a metal of the conductive CNTs dotted with the metal to the thiol groups on the substrate surface, wherein said conductive CNT dotted with the metal has a form of CNT-(CONH—$R_1$—S-M)r; (c) binding the conductive CNTs to the conductive CNTs attached to the substrate, to deposit the conductive CNTs; and (d) repeating the step (c), to increase the density of the conductive CNTs, wherein M represents a metal, r is a natural number greater than 1, and $R_1$ is selected from $C_{1-20}$ saturated hydrocarbons and unsaturated hydrocarbons.

* * * * *

UNITED STATES PATENT AND TRADEMARK OFFICE
CERTIFICATE OF CORRECTION

PATENT NO. : 7,670,831 B2
APPLICATION NO. : 10/860544
DATED : March 2, 2010
INVENTOR(S) : Sang Yup Lee It is certified that error appears in the above-identified patent and that said Letters Patent is hereby corrected as shown below:

Column 18, line 7: "$CNT\text{-}(CONH\text{-}R_1\text{-}S\text{-}M)r$" should be -- $CNT\text{-}(CONH\text{-}R_1\text{-}S\text{-}M)_r$ --.

Signed and Sealed this

Sixteenth Day of November, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
tgtgccacct acaagctgtg sc                    22

<210> SEQ ID NO 2

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
cacagcttgt aggtggcaca                                              20
```